(12) United States Patent
Clavijo et al.

(10) Patent No.: US 11,878,116 B2
(45) Date of Patent: Jan. 23, 2024

(54) TRACHEO-BRONCHIAL SAMPLING DEVICE

(71) Applicant: Iowa State University Research Foundation, Inc., Ames, IA (US)

(72) Inventors: Maria J. Clavijo, Ames, IA (US); Kevin J. Brownfield, Ames, IA (US); John K. Jackman, Ames, IA (US); Bailey Arruda, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 301 days.

(21) Appl. No.: 16/949,491

(22) Filed: Oct. 30, 2020

(65) Prior Publication Data

US 2021/0128858 A1     May 6, 2021

Related U.S. Application Data

(60) Provisional application No. 62/929,236, filed on Nov. 1, 2019.

(51) Int. Cl.
| | | |
|---|---|---|
| *A61M 16/04* | (2006.01) | |
| *A61B 1/267* | (2006.01) | |
| *A61B 10/04* | (2006.01) | |
| *A61B 10/02* | (2006.01) | |

(52) U.S. Cl.
CPC ......... *A61M 16/0488* (2013.01); *A61B 1/267* (2013.01); *A61B 10/04* (2013.01); *A61B 2010/0216* (2013.01); *A61M 2205/02* (2013.01)

(58) Field of Classification Search
None
See application file for complete search history.

(56) References Cited

U.S. PATENT DOCUMENTS

| | | | | |
|---|---|---|---|---|
| 3,881,464 A | * | 5/1975 | Levene | A61B 10/0291 15/207.2 |
| 4,762,133 A | * | 8/1988 | Bayne | A61B 10/0291 600/572 |
| 5,137,030 A | * | 8/1992 | Darougar | A61B 10/02 600/570 |
| 5,462,063 A | * | 10/1995 | Kist | A61B 10/0291 600/570 |
| D614,292 S | * | 4/2010 | Anderson | D24/119 |
| 8,152,736 B2 | * | 4/2012 | Caillat | A61B 10/02 600/562 |

(Continued)

*Primary Examiner* — Benjamin S Melhus
(74) *Attorney, Agent, or Firm* — McKee, Voorhees & Sease, PLC

(57) ABSTRACT

A tracheal sampling device is used to collect or acquire cells from an animal, such as at or near the tracheo-bronchial or larynx of an animal. The device includes a flexible and elongated shaft or stem, and a collection member at a distal end of the device. The collection member could be a swab or other member to best collect mucus. The device is used by inserting the collection end into an animal to position the collection member at or near the cell collection site, which may be in or around the larynx. The collection member is removed after collecting cells, which can be reviewed, tested, or otherwise managed to determine the presence of a disease or other bacteria. The length of the shaft or stem allows for optimal positioning of the swab in a variety of animal species and ages. The device can be disposed after each use.

8 Claims, 11 Drawing Sheets

(56) References Cited

U.S. PATENT DOCUMENTS

| | | | |
|---|---|---|---|
| 8,475,394 B1* | 7/2013 | Stivers | A61B 10/02 600/572 |
| D809,140 S* | 1/2018 | Sasayama | D24/147 |
| D834,215 S* | 11/2018 | D'Aoust | D24/216 |
| 11,083,440 B2* | 8/2021 | Delio | A61B 5/097 |
| 2005/0284239 A1* | 12/2005 | Chuang | G01N 1/02 73/864 |
| 2008/0206740 A1* | 8/2008 | Skiffington | G01N 1/02 435/5 |
| 2008/0294067 A1* | 11/2008 | Zwart | A46D 1/0238 600/569 |
| 2009/0012425 A1* | 1/2009 | Dodge | A61B 10/0045 600/572 |
| 2009/0030341 A1* | 1/2009 | Kshirsagar | G01N 1/38 600/572 |
| 2011/0127177 A1* | 6/2011 | Hostettler | B01L 3/5082 264/254 |
| 2012/0310113 A1* | 12/2012 | Giddings | A61B 10/0045 600/572 |
| 2012/0329081 A1* | 12/2012 | Bennion | B01L 3/5023 435/8 |
| 2013/0116596 A1* | 5/2013 | Birnboim | A61B 10/0096 600/572 |
| 2014/0083213 A1* | 3/2014 | Triva | A61B 10/02 73/864 |
| 2014/0171828 A1* | 6/2014 | Blitzer | A61M 5/007 600/570 |
| 2014/0336528 A1* | 11/2014 | Sethi | A61B 10/0266 600/566 |
| 2015/0065915 A1* | 3/2015 | Jafri | A61B 10/04 600/569 |
| 2016/0038348 A1* | 2/2016 | Booth | A61F 13/00068 433/136 |
| 2016/0302776 A1* | 10/2016 | Adolphson | A61B 10/0096 |
| 2016/0317132 A1* | 11/2016 | Markowitz | A61B 10/02 |
| 2016/0367227 A1* | 12/2016 | Triva | C12M 33/02 |
| 2017/0049422 A1* | 2/2017 | Ferris | A61B 10/0096 |
| 2017/0065261 A1* | 3/2017 | Ching | A61B 10/02 |
| 2017/0215568 A1* | 8/2017 | Kim | A46B 9/06 |
| 2018/0161020 A1* | 6/2018 | Friedlander | A61B 10/02 |
| 2018/0243735 A1* | 8/2018 | Mantlo | B01L 3/021 |
| 2019/0307437 A1* | 10/2019 | Rincón Orozco | A61B 17/42 |
| 2020/0281572 A1* | 9/2020 | Andersson | A61B 10/0045 |
| 2020/0305851 A1* | 10/2020 | Gilbert | A61B 10/0291 |
| 2022/0287690 A1* | 9/2022 | Gilbert | A61B 10/0283 |

* cited by examiner

TRACHEO-BRONCHIAL SAMPLING DEVICE

CROSS REFERENCE TO RELATED APPLICATIONS

This application claims priority under 35 U.S.C. § 119 to provisional patent application U.S. Ser. No. 62/929,236, filed Nov. 1, 2019. The provisional patent application is herein incorporated by reference in its entirety, including without limitation, the specification, claims, and abstract, as well as any figures, tables, appendices, or drawings thereof.

FIELD OF THE INVENTION

The invention is directed generally to the field of animal health testing. More particularly, but not exclusively, the invention is directed towards a sampling device for use with large animals to better acquire a sample in a desired location for testing of potential diseases.

BACKGROUND OF THE INVENTION

*Mycoplasma hyopneumoniae* (Mhp), the primary pathogen of enzootic pneumonia, occurs worldwide and causes major economic losses to the pig industry. The pathogen adheres to and damages the ciliated epithelium of the respiratory tract. Affected pigs usually show chronic coughing, are more susceptible to other respiratory infections and have a reduced performance. Moreover, Mhp plays a key role in the Porcine Respiratory Disease Complex (PRDC) through interactions with several other respiratory pathogens.

Piglets can become infected with Mhp during the suckling period and many studies have shown Mhp-positive animals from weaning onwards. Moreover, once infected with Mhp, animals can excrete the pathogen over a long period of time, with total clearance lasting till 254 days post-infection. This implies that infected gilts could carry Mhp well across their first pregnancy into their first lactation cycle, infecting their offspring with Mhp in early life.

Thus, Mhp continues to be a significant cause of respiratory disease in grow-finish swine populations, with reported annual industry losses of $400 million. Effective prevention and control of Mhp requires the implementation of accurate and comprehensive diagnostic protocols. Given that Mhp establishes infection in the lower airway, tracheo-bronchial mucus appears to be the most sensitive sample, compared to oral fluids and upper respiratory swabs.

Effective prevention and control of *M. hyopneumoniae* requires the implementation of accurate and comprehensive diagnostic protocols. Given that *M. hyopneumoniae* establishes infection in the lower airway (ciliated epithelium of the respiratory track) mucus appears to be the most sensitive sample, compared to oral fluids and upper respiratory swabs, such as laryngeal swans Surveillance of Mhp in live pigs provides relevant information on the level of infection and spread within farms, which is a key element when designing control and elimination efforts. Several diagnostic tools and sampling techniques have been developed for detection of Mhp. The most common diagnostic test employed for health monitoring is serum based antibody-ELISAs. However, the utility of serological assays for Mhp can be hindered by the highly variable time lapse between infection (~4-8 weeks) and antibody production, the limited correlation between a positive assay and disease, inability to differentiate natural infection from vaccination and antibody cross-reactions with other mycoplasmas.

Thus, it is challenging to interpret results based on the individual or at the herd level. Detection of the antigen via qPCR is also available and routinely used, however, the challenge arises from the variation in sensitivity levels depending on the sampling site and timing of the infection. For example, oral fluids, while convenient to collect are not sensitive if there are no clinical signs present in the pigs (i.e. cough). Similarly, studies have shown a poor sensitivity of nasal and tonsil swabs for detection of Mhp. Tracheo-bronchial samples have been shown to be the most sensitive method for Mhp diagnosis in live pigs. Although more labor intensive, trachea-bronchial sampling has been recently adopted by swine producers and practitioners for their surveillance programs.

However, there are currently no commercially available tracheo-bronchial sampling devices. Instead, field veterinarians have relied on "quick and dirty" approaches to carry out tracheo-bronchial samplings by using either modified tracheal catheters or artificial insemination rods, which have not been properly validated and lack the necessary characteristics to collect adequate amounts of sample (i.e. tracheo-bronchial mucus). The complicated biology and epidemiology of Mhp, coupled with a lack of rapid and accurate diagnostic tools hinders adequate diagnosis and control of Mhp.

Therefore, there is a need in the art for developing a practical, sensitive, low-cost, and safe tracheo-bronchial sampling device.

SUMMARY OF THE INVENTION

The following objects, features, advantages, aspects, and/or embodiments, are not exhaustive and do not limit the overall disclosure. No single embodiment need provide each and every object, feature, or advantage. Any of the objects, features, advantages, aspects, and/or embodiments disclosed herein can be integrated with one another, either in full or in part.

Therefore, it is a primary object, feature, and/or advantage of the invention to improve on or overcome the deficiencies in the art.

It is another object, feature, and/or advantage to provide a disposable tracheo-bronchial sampling device for the detection of Mhp in live animals.

It is yet another object, feature, and/or advantage to provide a tracheo-bronchial sampling device that is sensitive to and easily implemented.

It is still another object, feature, and/or advantage to provide a tracheo-bronchial sampling device that is positionable in the trachea of a live animal.

It is a further object, feature, and/or advantage to provide a practical, sensitive, low-cost and safe tracheo-bronchial sampling device.

It is still a further object, feature, and/or advantage to provide a sampling device that can vary in dimension to account for animals of different age and/or species.

It is still yet a further object, feature, and/or advantage of the invention to provide a safe, cost effective, and durable apparatus.

It is still yet a further object, feature, and/or advantage of the invention to practice methods which facilitate use, manufacture, assembly, maintenance, and repair of the apparatus accomplishing some or all of the previously stated objectives.

The previous objects, features, and/or advantages of the present invention, as well as the following aspects and/or embodiments, are not exhaustive and do not limit the overall disclosure. No single embodiment need provide each and every object, feature, or advantage. Any of the objects, features, advantages, aspects, and/or embodiments disclosed herein can be integrated with one another, either in full or in part.

According to some aspects, a tracheal sampling device includes a flexible, elongated shaft, and a collection member at an end of the flexible, elongated shaft, with the collection member comprising a hollow member with a plurality of annularly-spaced slots to aid in collecting a sample.

According to at least some aspects, the device further comprises a handle at an end of the shaft opposite the collection member.

According to at least some aspects, the device further comprises a handle integrally formed along the length of the shaft.

According to at least some aspects, the collection member comprises a hydrophilic material.

According to at least some aspects, the shaft is a hollow tube.

According to at least some aspects, the collection member is attached to the shaft at a predefined fracture point, wherein the collection member can be removed at the predefine fracture point after making a sample collection.

According to some aspects of the present disclosure, a tracheal sampling device comprises a handle; a flexible, elongated shaft extending from the handle; and a swab extending from a distal end of the flexible, elongated shaft.

According to some additional aspects of the disclosure, a cap is positioned at the swab to cover at least a portion of the swab.

According to some additional aspects of the disclosure, the swab comprises a flocked swab.

According to some other aspects of the disclosure, the flocked swab comprises a stem extending from the flexible, elongated shaft and flocking at a distal end of the stem.

According to some additional aspects of the disclosure, the swab is integral with the flexible, elongated shaft.

According to some additional aspects of the disclosure, the swab is removable from the flexible, elongated shaft.

According to some additional aspects of the disclosure, the flexible, elongated shaft is solid.

According to some additional aspects of the disclosure, the flexible, elongated shaft is tubular.

According to some additional aspects of the disclosure, the handle and flexible, elongated shaft comprise ultra-high molecular weight polyethylene (UHMWPE).

According to some additional aspects of the disclosure, the handle is integral with the flexible, elongated shaft.

According to some additional aspects of the disclosure, the handle is removable from the flexible, elongated shaft.

According to additional aspects, a tracheal sampling device includes an elongated shaft comprising a flexible material and being hollow from a first end to a second end, and a collection tip at a distal end of the elongated shaft, said collection tip being hydrophilic and comprising a hollow member having a plurality of channels or slots at a distal end thereof.

According to at least some aspects and/or embodiments, the elongated shaft comprises a predefined fracture point near the distal end of the shaft to allow the collection tip to be removed via the predefined fracture point.

According to at least some aspects and/or embodiments, the device further comprises a handle associated with the shaft, said handle positioned at the first end of the elongated shaft.

These and/or other objects, features, advantages, aspects, and/or embodiments will become apparent to those skilled in the art after reviewing the following brief and detailed descriptions of the drawings. Furthermore, the present disclosure encompasses aspects and/or embodiments not expressly disclosed but which can be understood from a reading of the present disclosure, including at least: (a) combinations of disclosed aspects and/or embodiments and/or (b) reasonable modifications not shown or described.

BRIEF DESCRIPTION OF THE DRAWINGS

Several embodiments in which the present invention can be practiced are illustrated and described in detail, wherein like reference characters represent like components throughout the several views. The drawings are presented for exemplary purposes and may not be to scale unless otherwise indicated.

Figure 1:
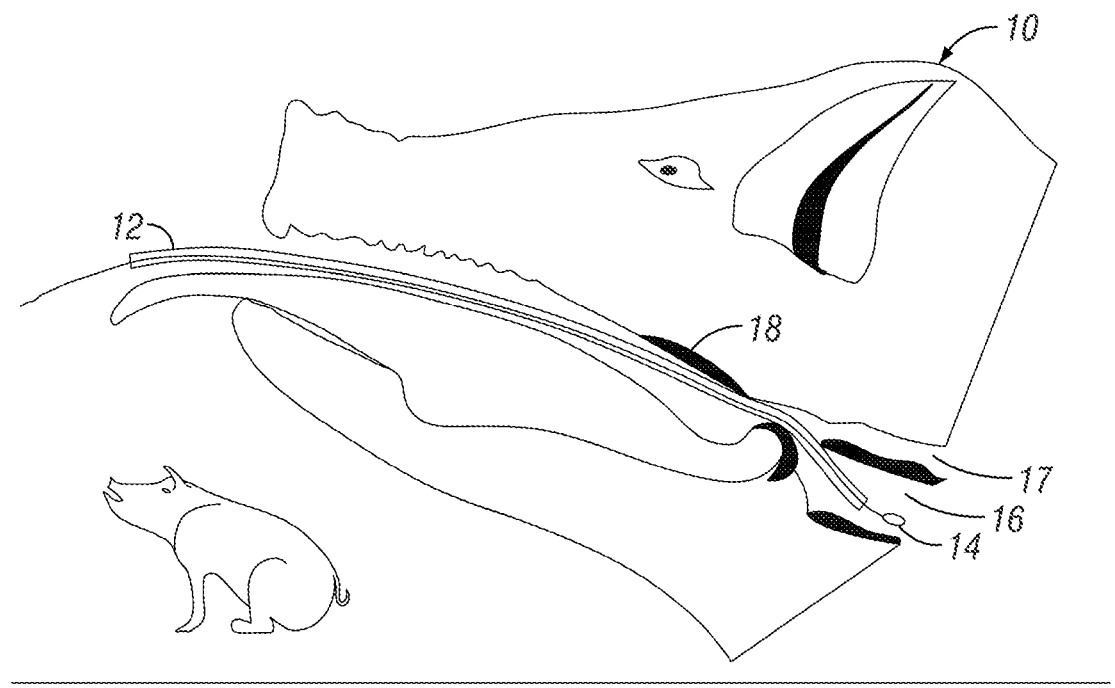
FIG. 1 is a schematic view of a swab insertion into an animal.

An artisan of ordinary skill need not view, within isolated figure(s), the near infinite number of distinct permutations of features described in the following detailed description to facilitate an understanding of the present invention.

DETAILED DESCRIPTION OF THE INVENTION

The following definitions and introductory matters are provided to facilitate an understanding of the present invention. Unless defined otherwise, all technical and scientific terms used herein have the same meaning as commonly understood by one of ordinary skill in the art to which embodiments of the present invention pertain.

The terms "a," "an," and "the" include both singular and plural referents. The term "or" is synonymous with "and/or" and means any one member or combination of members of a particular list.

The terms "invention" or "present invention" as used herein are not intended to refer to any single embodiment of the particular invention but encompass all possible embodiments as described in the specification and the claims.

The term "about" as used herein refers to slight variations in numerical quantities with respect to any quantifiable variable. One of ordinary skill in the art will recognize inadvertent error can occur, for example, through use of typical measuring techniques or equipment or from differences in the manufacture, source, or purity of components. The claims include equivalents to the quantities whether or not modified by the term "about."

The term "configured" describes an apparatus, system, or other structure that is constructed to perform or capable of performing a particular task or to adopt a particular configuration. The term "configured" can be used interchangeably with other similar phrases such as constructed, arranged, adapted, manufactured, and the like.

Terms characterizing a sequential order (e.g., first, second, etc.), a position (e.g., top, bottom, lateral, medial, forward, aft, etc.), and/or an orientation (e.g., width, length, depth, thickness, vertical, horizontal, etc.) are referenced according to the views presented. Unless context indicates otherwise, these terms are not limiting. The physical configuration of an object or combination of objects may change without departing from the scope of the present invention.

As would be apparent to one of ordinary skill in the art, mechanical, procedural, or other changes may be made without departing from the spirit and scope of the invention. The scope of the invention is defined only by the appended claims, along with the full scope of equivalents to which such claims are entitled.

The need for a quick, reliable, portable, and safe sampling device to acquire cells for sampling for detection of *Mycoplasma hyopneumoniae* (Mhp) is clear in the art. The evidential transmission rate of Mhp shows that this organism usually spreads slowly within pig populations, making it hard to detect early. More interestingly, looking at the variation between strains shows that if some of these circulating isolates enter a population the likelihood that they will spread within a population is low. This complicates diagnostics.

Figure 2:
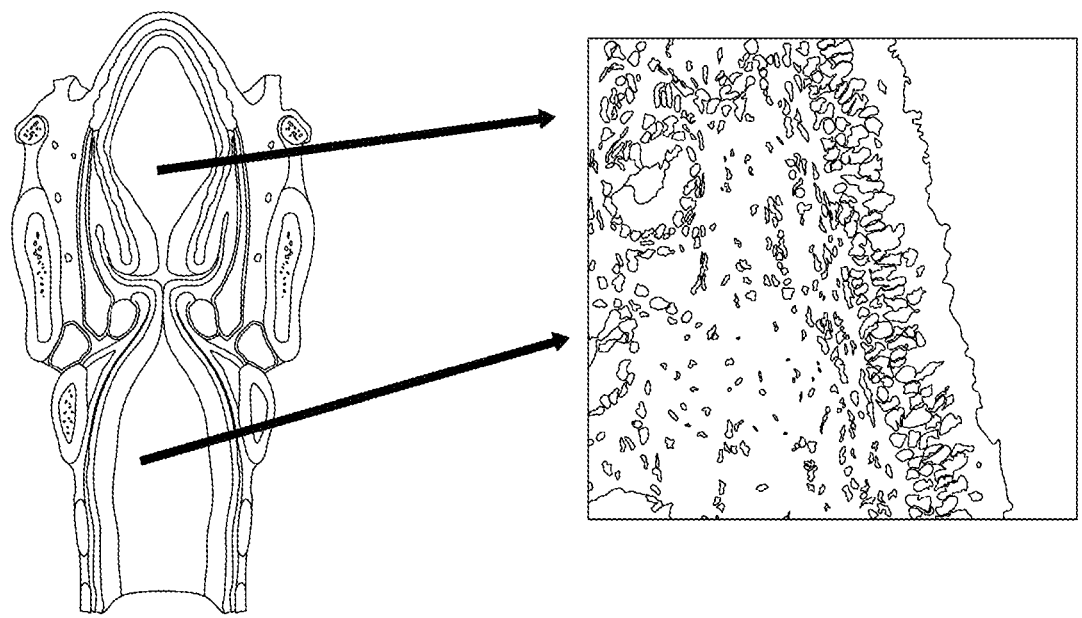
FIG. 2 is a schematic view of the anatomy of an animal showing the location for tracheo-branchial sampling.

One way to test for Mhp is to swab a desired area of an animal, such as a pig. Previously, as shown in FIG. 1, a pig 10 can be swabbed at a tracheal position 16 or a laryngeal location. For example, FIG. 2 shows the anatomy of a pig 10, such as shown in FIG. 1, including the location of proposed or desired swabbing. As shown in FIG. 2 (right side), a portion of the larynx is shown. More particularly, the right side is a section of a larynx, the cartilaginous box into which the epiglottis opens. This is shown at right, cut longitudinally. The pharyngeal end of the larynx is at the top of this low-power view. The larynx is a box constructed of plates of hyaline and some elastic cartilage, articulated together with CT. The muscles controlling the shape of the box insert onto the cartilage. On the oral cavity side of the glottis, the lining of the system is stratified squamous, and several laryngeal tonsils can be seen. Once past the entrance there's an abrupt transition from stratified squamous epithelium of the oral cavity to respiratory epithelium.

There is noted sensitivity differences between Laryngeal swabs and Tracheal swabs. Tracheal swab sampling method is more sensitive for Mhp detection during chronic infection. However, there is difficulty and cost of tracheal sample collection is comparable with laryngeal samples. As such, tracheal swabs are the preferred sample following acute infections.

Referring back to FIG. 1, tracheal swabbing itself is not new. As shown, an endotracheal tube 12, modified tracheal catheters, artificial insemination rods, or other "quick and dirty" approaches that have not been properly validated and lack the necessary characteristics to collect adequate amounts of sample have been used in the field. The complicated biology and epidemiology of Mhp coupled with a lack of rapid and accurate diagnostic tools hinders adequate diagnosis and control of Mhp. As disclosed herein, the tools are not sufficient to collect the required specimen and are not made to be positioned as shown in FIG. 1 past the tonsil 18 and esophagus 17 and positioned the swab 14 in the trachea 16. The makeshift tools can break and injure an animal, cause discomfort, may not be sterile, or may not properly collect enough of a sample for adequate testing.

Figure 3:
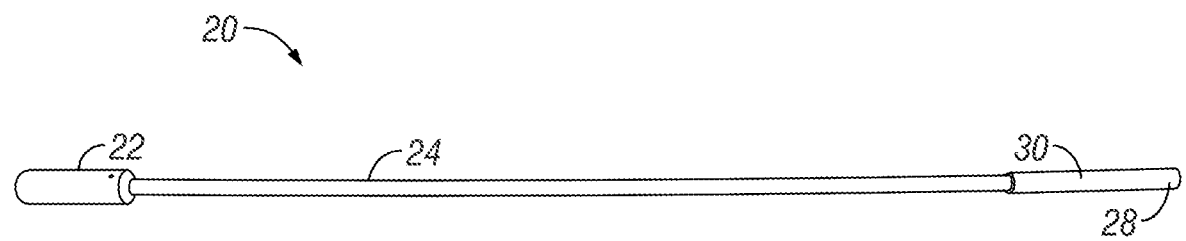
FIG. 3 is a view of a sampling device according to aspects of the disclosure.
Figure 4:
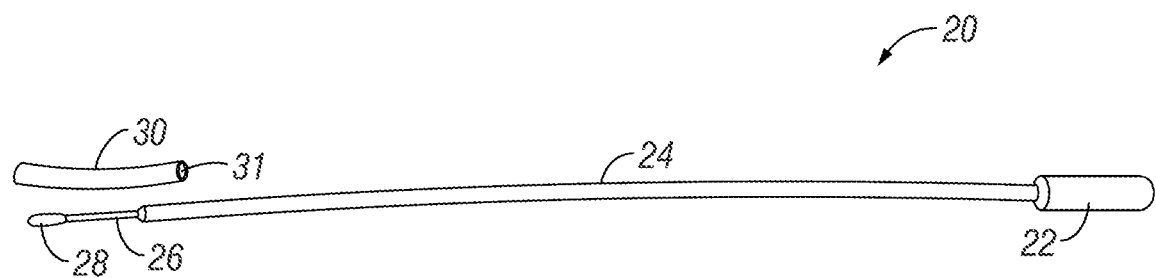
FIG. 4 is a view of the device of FIG. 3 without a cover.

Therefore, aspects of the invention include a novel tracheal sampling device 20, which is shown in FIGS. 3 and 4. At its core, the sampling device 20 shown in FIGS. 3 and 4 comprises three parts: i) sterile flocked swab 28 with cap 30; ii) a flexible 17-inch long shaft 24; and iii) a handle 22. The prototype, according to some embodiments, is 21-inches long from attachment piece to handle (25-inches including swab). The length allows for sampling of grow-finish pigs and adult sows and boars. FIG. 3 shows the device 20 with the cap 30 on, and FIG. 4 shows the cap 30 off.

Figure 5:
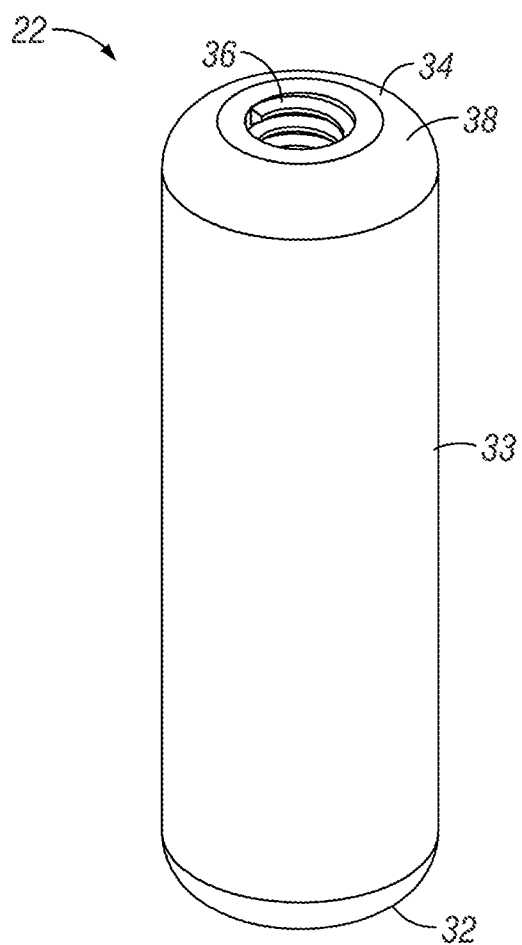
FIG. 5 is a view of a handle of the sampling device.
Figure 6:
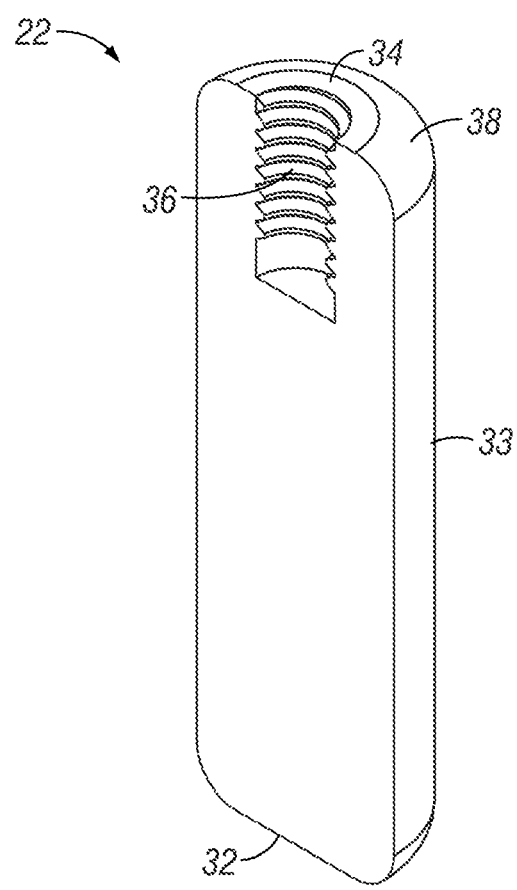
FIG. 6 is a sectional view of the handle of FIG. 5.

The handle 22, shown in more detail in FIGS. 5 and 6, can comprise ultra-high molecular weight polyethylene (UHMWPE), high-density polyethylene (HDPE), thermoplastics, rubbers, silicone, or other materials suited for fabricating a wide range of geometries using standard manufacturing processes, such as injection molding and machining. According to any of the embodiments disclosed herein, the handle can be extruded raw material that is machined or can be injection molded. As shown in FIGS. 5 and 6, the handle is generally cylindrically-shaped, and has a first end 32, a second end 34, and a body 33 therebetween. According to some embodiments, the handle 22 may be approximately 2-inches long, but this can vary and is not to be limiting on the invention. In addition, the first and second ends 32, 34 are shown to include a fillet 38. Again, this is not limiting, and the shoulder could be filleted, chamfered, beveled, edged, or otherwise.

In addition, the handle 22 includes an interior threading 36, which may also be referred to as female or receiving threads. This is best shown in FIG. 6, where the threads 36 extend axially a distance from the second end 34 and towards, but not reaching the first end 32. The exact length of the threading should be sufficient to attach the shaft or stem 24, as will be understood, and should not be limiting on the invention itself. However, according to some embodiments, the threads extend approximately 0.50-inches into the handle. The handle 22 is used generally to hold and control the sampling device 20 as it is used in the field.

Figure 7:
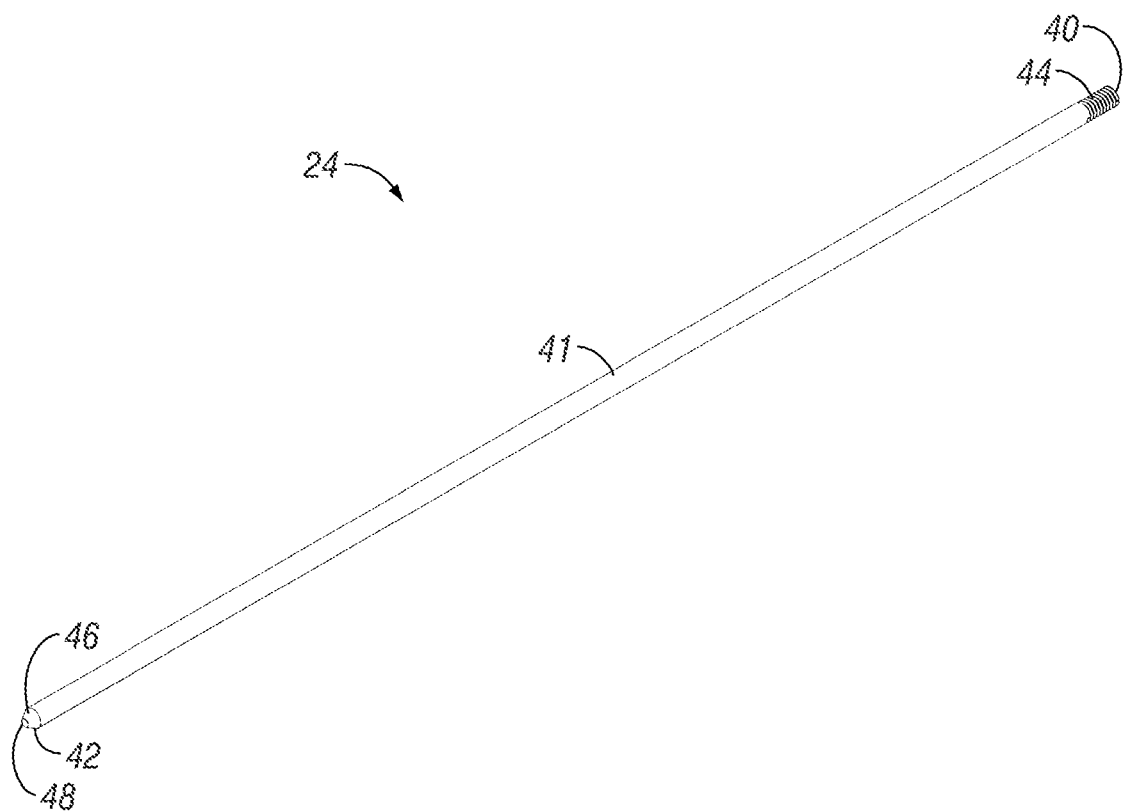
FIG. 7 is a view of the stem section of the sampling device.
Figure 8:
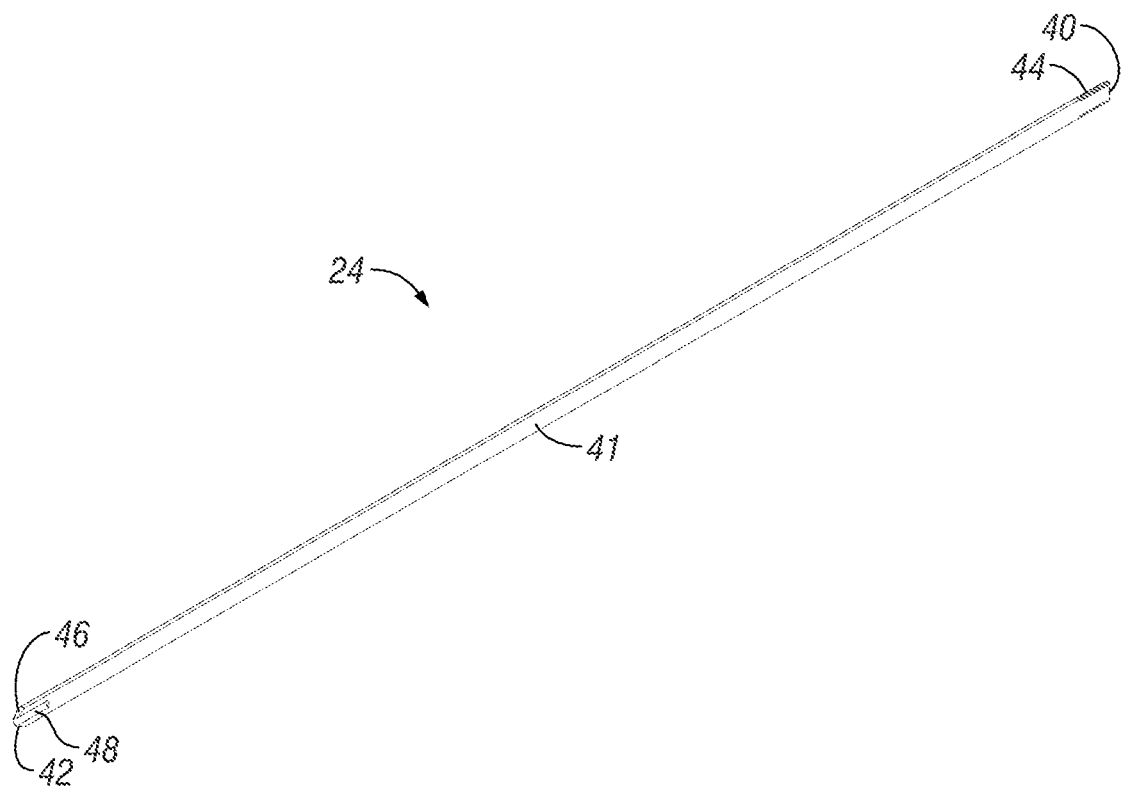
FIG. 8 is a sectional view of the stem of FIG. 7.

The shaft or stem 24 is shown in more detail in FIGS. 7 and 8, and can also comprise ultra-high molecular weight polyethylene (UHMWPE), high-density polyethylene (HDPE), thermoplastics, isoprene or other rubbers, silicone, combinations of the same, or other materials suited for fabricating a wide range of geometries using standard manufacturing processes, such as injection molding and machining. Still further, it is to be appreciated that the materials be chosen based upon their flexibility or elasticity, such that the shaft 24 is able to be manipulated through different tracheals. The shaft 24 is longer than the handle 22, and is inserted into the animal being tested. The length of the shaft 24 should be sufficient to reach the tracheal region of the animal being tested, and therefore, may take varying lengths depending on species, age, sex, and other variations. According to the exemplary device 20 shown in the figures and used with pigs, the handle may have a length of 17-inches, and a diameter of approximately 0.25-inches.

The shaft 24 includes a first end 40, second end 42, and a body 41 therebetween. Positioned generally at the first end 40 of the shaft 24 is an exterior threaded portion 44, also known as a male threading. The threading 44 of the shaft 24 is configured to match and connect with the threading 36 of the handle 22. Therefore, the radius of the threading can be chosen to allow for connection of the components. The threading 44 on the shaft 24 extends a length from the first end 40 towards the second end, and, while not limiting on the invention, can be approximately 0.44-inches in length.

Thus, the handle 22 and the shaft 24 can be connected to form a single unit. In addition, the components could be extruded and machined, injected and machined, injected, or otherwise formed as a single, integral unit that does not require or include corresponding threading portions.

According to some embodiments, the shaft 24 is a solid material except at the recess 48. However, it should be appreciated that the shaft 24 could be tubular in nature, which would reduce the weight and amount of material for the shaft 24, reducing the cost thereof. The tubular nature could also provide a passage to aid in the animal being tested to breathe, as there would be an aperture while the device 20 is positioned in the tracheal region of the animal. The handle 22 could also be tubular or solid.

For example, when the stem 24 is hollow, as may be preferred, the handle 22 can be removed all together, or could be moved to be integral with the stem 24. The hollow stem 24 allows for better breathing of the animal being swabbed.

The second end 42 of the shaft 24 includes a chamfer 46, which could also be a bevel, fillet, or other shoulder finishing. In addition, there is a recess formed at the second end 42 that extends into the body 41 of the shaft 24 towards the first end 40. The recess 48, shown best in FIG. 8, receives a portion of the swab 28, such as the stem 26 therein. This allows the swab 28 to be connected to the shaft for use. The recess 48, therefore, can be near infinite sizes in terms of diameter and length, but for purposes of the embodiment shown in the figures, can be 0.10-inches in diameter and can extend approximately 0.50-inches into the shaft 24. It should be appreciated that the recess can include additional features to aid in securing the stem 26 of the swab 28 therein, such as but not limited to, knurling in the recess or on the stem, adhesives, glues, tolerancing, or other mechanical or material manners to aid in holding the stem 26 in place in the recess 48.

Referring back to FIGS. 3 and 4, a swab 28 is shown. The swab 28 may be a flocked swab at the distal end of a stem 26. The flocked swab generally is a specimen collection device with tufts of polyester material attached to the end of a plastic shaft; used to collect specimens of bacterial and viral pathogens. Flocking refers to a process of applying (multi length fibers)—called flocking—to an adhesive-coated surface to provide for enhanced sample collection. Flocked swabs are an excellent choice for use with rapid diagnostic tests because of their ability to better collect cells or organisms at the collection site and rapid release of entire cells. While a flocked swab is preferred, it should be appreciated that other swabs, including cotton swabs and other specimen collecting materials can be used at or near the distal end of the stem 26.

The stem 28 is used to connect the swab 28 to the shaft 24 and handle 22. The stem 28 can also comprise ultra-high molecular weight polyethylene (UHMWPE), high-density polyethylene (HDPE), thermoplastics, or other materials suited for fabricating a wide range of geometries using standard manufacturing processes, such as injection molding and machining. Furthermore, the stem 28 can comprise other plastics, paper, wood, or the like, which can be connected to the shaft 24.

As disclosed, the stem 28 is connected to the shaft 24 such as be inserting a portion of the stem 28 into the recess 48 of the shaft 24. The stem 28 can be held in place in a number of ways, including, but not limited to, machined portions (e.g., knurling or the like), friction fit (i.e., tolerancing), glues or other adhesives, or some combination thereof. In addition, it is contemplated that the stem 28 comprise the same integral piece as the shaft 24 and handle 22, and be machined to the desired size for flexibility and other functional purposes.

Also shown in FIGS. 3 and 4 is a cap 30. The cap is shown to be a tubular piece of material that is sized to go over and cover the swab 28. This preserves the swab 28 until the device is to be used, and can keep the sterilized, flocked swab sterilized until such time as it is to be used. The cap can have a closed end at the distal portion and an open opposite end 31 to allow for the swab to be inserted therein, thus preserving and protecting the swab until use. In addition, the cap 30 can comprise any of the materials of any of the other components of the sampling device 20.

Figure 9:
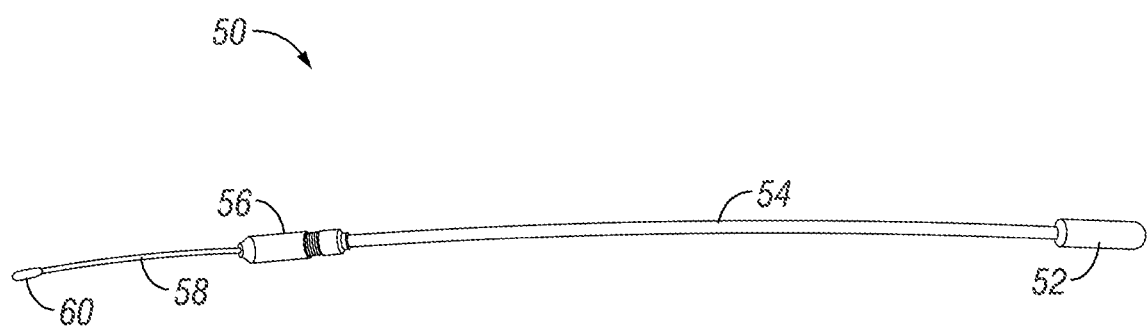
FIG. 9 is a view of another sampling device according to aspects of the disclosure.

FIG. 9 is another embodiment of a sampling device 50, which includes many of the same or similar components as that described herein. This includes a handle 52, a shaft 54 connected to or formed with the handle 52, and a swab 60 connected to and extending from the shaft 54. However, in the embodiment of FIG. 9, the swab 60 is not inserted into the shaft 54, but is connected via an extension or attachment 56. The extension covers at least a portion of the shaft 54, with a flocked swab 60 at a distal end of a stem 58.

Either embodiment as shown and/or described may be disposable and configured for a one-time use with a pig for sample collecting for testing. The devices are made with minimal material, which keeps the devices inexpensive and allows for the one-time use to be cost-efficient and comparable to other, comparable items currently used, while providing advantages and higher safety than said comparable items.

Still further variations, options, features, components, and/or the like could be used with any of the embodiments as shown and described herein. For example, it is contemplated that the stem 26 of swab 28 could be completely inserted into the shaft 24. This could reduce the risk that the swab will break while sampling. For example, in such a situation, there would be little to no stem 26 extending from the shaft 24, and instead, the shaft could essentially or substantially end with the swab 28 at the distal end of the shaft. There could be some stem exposed, but keeping this minimal can aid in the mitigation of the stem breaking.

Figure 11:
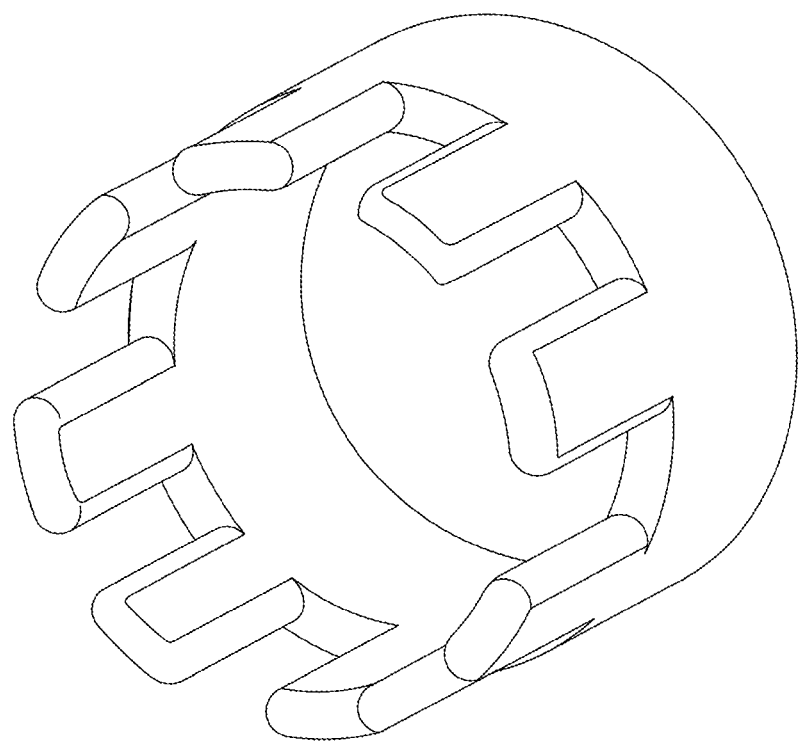
FIG. 11 is an isometric view of a slotted sampling tip used with a sampling device according to aspects of the invention.

Still further, as disclosed herein, it is contemplated that the shaft 24 be hollow. In some embodiments, the swab 28 could be replaced with a detachable plastic piece, such as a slotted cap 70 (see, e.g., FIG. 11). As shown in the figure, the slotted cap could be approximately two-inches long, and has increased surface tension making it more hydrophilic. The cap 70 also includes a number of slots or channels 72. According to at least some embodiments, the indentations/slots/channels 72 are approximately $1/16^{th}$ of an inch, which aids in capturing mucus during insertion and collection. The slotted cap 70 can comprise a hydrophilic plastic polymer. Note that the cap is hollow, and includes open ends opposite one another, with slots formed in the distal end of the cap. The exact number of slots and sizes and shapes thereof are not to be limiting on the device, and it should be appreciated that a device such as the cap shown would allow the pigs to breathe easier during sampling while maintaining the ability to capture the mucus. The cap, as shown in the figure, could be placed directly at the distal/second end of the shaft, and as disclosed, when the shaft is also hollow, will allow for a passage that the breath of a test animal could pass through.

The slots could be used to collect the sample for later testing and diagnostics. Still further, the hydrophilic plastic polymer tip, or any tip, could be removed from the shaft and placed into a transport tube for testing. The hollow variation also allows for mucus to accumulate in the inside of the tube. The bacterium for testing is present in the mucus.

Still further possible variations to any of the embodiments include the addition of a protective sheath to the rod. This would allow for collection of a cleaner sample for increase success of bacterial culture and isolation. The handle could also be placed lower on the shaft, which would give an operator a better grip on the sampling device.

EXAMPLE

Figure 10:
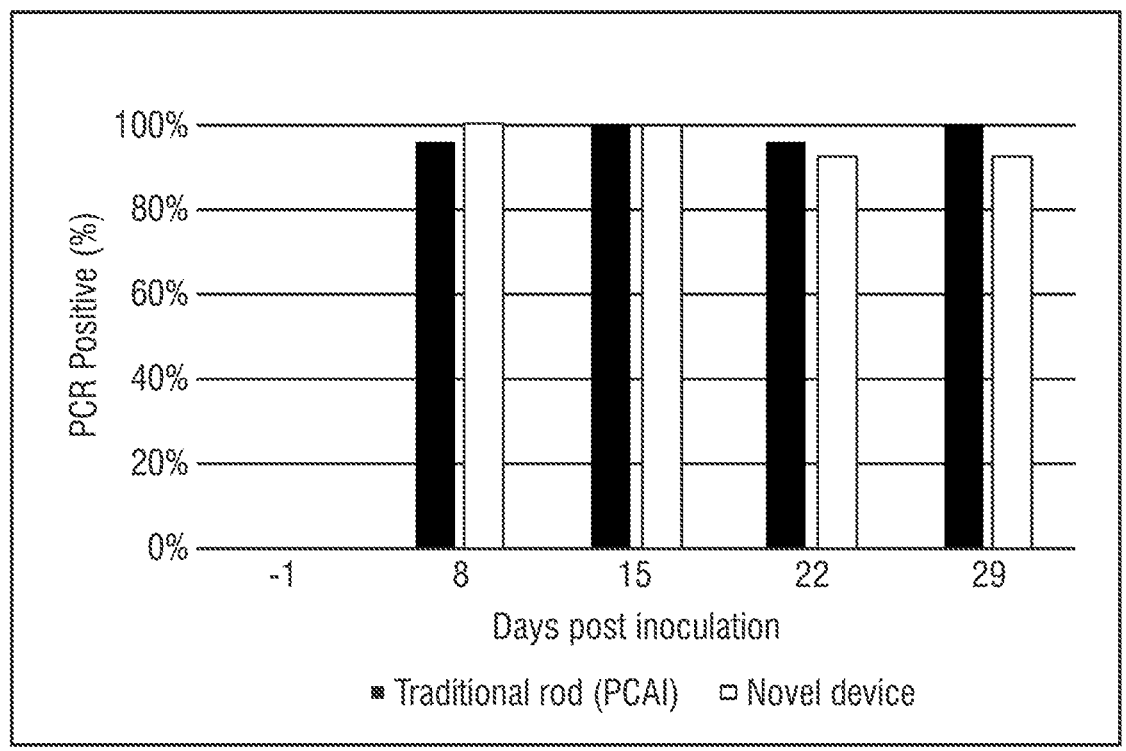
FIG. 10 is a graph showing percentage PCR positive by sampling device at 0, 8, 15, 29 days post-inoculation.

To test the embodiment of the sampling device 20 shown in FIGS. 3 and 4, a side by side comparison was carried out using the traditional catheter (PCAI rod) and the sampling device 20 on pigs (n=24) experimentally inoculated with Mhp. In brief, the pigs were restrained with a snare and were subjected to two samplings; traditional catheter followed by the sampling device 20. The pig's mouth was held open with a mouth speculum and each device was inserted deeply into the trachea as the pig inspired, then rotated and moved up and down against the trachea. A total of 96 samples were collected at different time points (0, 8, 15, and 29 days post-inoculation). The sampling device 20 of the present disclosure was easy to use and practical. The handle 22 provided better grip on the device 20. Preliminary results showed nearly identical detection rates between devices, with a proportional agreement of 96.6% (see, e.g., FIG. 10). No statistical difference was observed between mean Ct values from the two devices (ANOVA; F=0.0.3; df=1; p value=0.85). Likewise, no statistical difference was observed between medians Ct values (Kruskall-Wallis; chi-squared=0.22; df=1; p value=0.65). See, e.g., Table 1 below.

TABLE 1

*M. hyopneumoniae* mean and median Ct values by device type

| Type of Device | Observations | Mean Ct (positives) | Median Ct (positives) | s.d. | Min | Max |
| --- | --- | --- | --- | --- | --- | --- |
| Traditional (PCAI rod) | 120 | 22.94$^a$ | 21.64$^a$ | 4.45 | 14.6 | 33.7994 |
| Novel device | 120 | 23.11$^a$ | 226$^a$ | 3.868 | 16.745 | 34.441 |

Values in a column suffixed with different letters are significantly different from each other at P < 0.05.

Therefore, a novel sampling device has been shown and described. The device includes numerous improvements over that which is currently known and used. Such improvements include, but are not limited to, a low cost, safe, sterile, flexible, and disposable device that is able to be positioned in the ideal location (e.g., tracheal region) of an animal to test for Mhp and/or other illnesses, bacteria, or otherwise. While the invention includes numerous variations, it should be appreciated and apparent to those skilled in the art that variations obvious to those skilled in the art are to be considered a part of the present disclosure.

The invention claimed is:

1. A tracheal sampling device, comprising:
    a flexible, elongated shaft;
    and a collection member at an end of the flexible, elongated shaft,
    the collection member comprising a hollow member having an open interior from a first end of the collection member to a second end of the collection member in a longitudinal direction
    and comprising a plurality of circumferentially-spaced slots around a periphery of the collection member at a distal end of the collection member,
    wherein said plurality of slots are configured to aid in collecting a tissue sample;
    wherein said plurality of circumferentially-spaced slots comprise a crenellation;
    wherein the collection member and the plurality of slots form a crenellated cap on the sampling device,
    the crenellated cap forming a distalmost extent of the sampling deice such that, via a position of the hollow member, the collection member is configured to only collect the tissue sample around the periphery, the periphery being only on a distally oriented circumferential edge of the collection member;
    and where, via the position of the hollow member, an entirety of an interior central volume of the shaft and of the collection member from a proximal-most extent of the device to the distalmost extent of the device is hollow such that the sampling device is configured to collect the tissue sample while simultaneously permitting air flow through an entire length of the sampling device such that a subject is able to breathe through the sampling device while the sampling device samples the subject.

2. The tracheal sampling device of claim 1, further comprising a handle at a proximal end of the shaft opposite the collection member.

3. The tracheal sampling device of claim 1, further comprising a handle integrally formed along the flexible, elongated shaft.

4. The tracheal sampling device of claim 1, wherein the collection member comprises a hydrophilic material.

5. The tracheal sampling device of claim 1, wherein the collection member is attached to the shaft at a predefined fracture point, wherein the collection member can be removed at the predefine fracture point after making a sample collection.

6. A tracheal sampling device, comprising:
    an elongated shaft comprising a flexible material and being hollow from a first end of the shaft to a second end of the shaft;
    and a collection tip at a distal end of the elongated shaft,
    said collection tip being hydrophilic and comprising a hollow member and comprising a plurality of channels or slots around a periphery of the collection tip at a distal end thereof;
    and wherein said plurality of channels or slots comprises a crenellated pattern
    wherein the collection member and the plurality of slots form a crenellated cap on the sampling device,
    the crenellated cap forming a distalmost extent of the sampling deice such that, via a position of the hollow member, the collection member is configured to only collect a tissue sample around the periphery, the periphery being only on a distally oriented circumferential edge of the collection member;
    and where, via the position of the hollow member, an entirety of an interior central volume of the shaft and of the collection member from a proximal-most extent of the device to the distalmost extent of the device is hollow such that the sampling device is configured to collect the tissue sample while simultaneously permitting air flow through an entire length of the sampling device such that a subject is able to breathe through the sampling device while the sampling device samples the subject.

7. The tracheal sampling device of claim 6, wherein the elongated shaft comprises a predefined fracture point adjacent the distal end of the shaft to allow the collection tip to be removed via the predefined fracture point.

8. The tracheal sampling device of claim 6, further comprising a handle associated with the shaft, said handle positioned at the first end of the elongated shaft.

* * * * *